Feb. 19, 1935. G C THOMAS JR Plant Pat. 122
VARIETY OF ROSE
Filed Feb 24, 1934
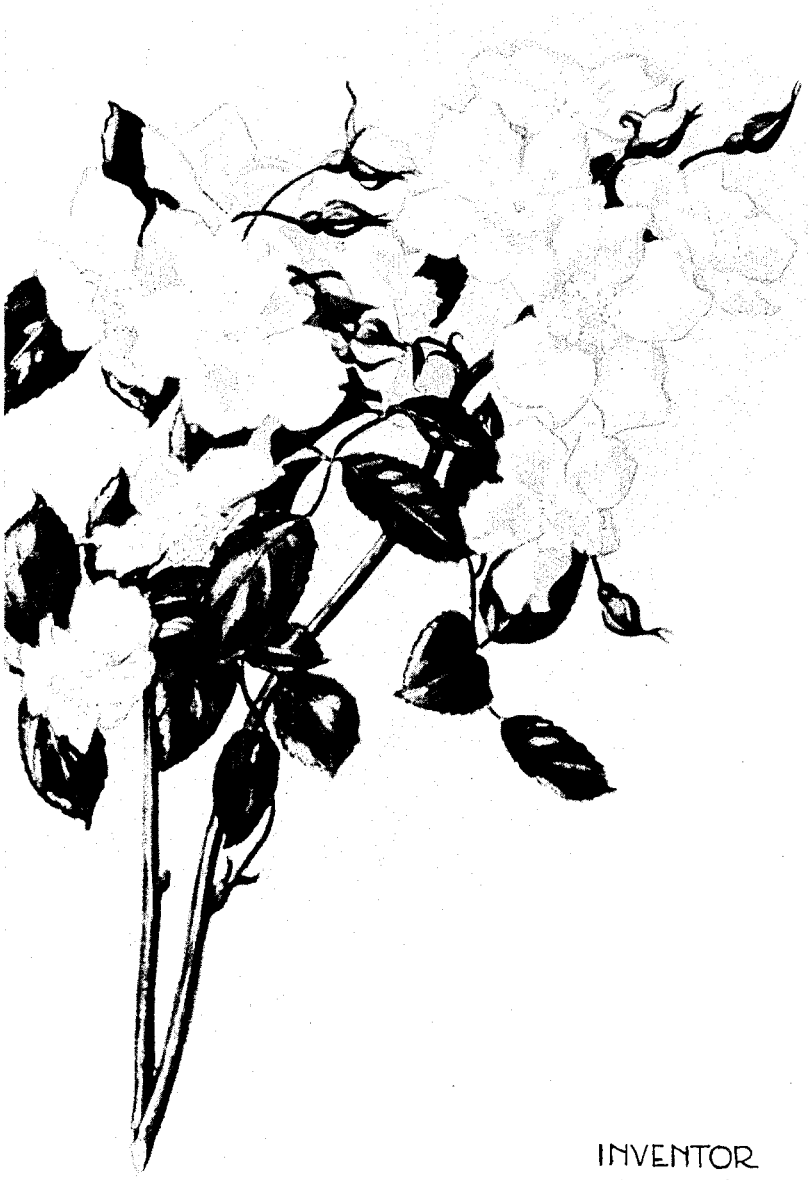
INVENTOR
GEORGE C. THOMAS, JR., DEC'D, BY
JOSEPHINE MOORHEAD THOMAS GARDNER &
GEORGE C. THOMAS III,
EXECUTORS
PLANT PATENT AGENT
Orville M. Kile Patented Feb. 19, 1935

Plant Pat. 122

UNITED STATES PATENT OFFICE

122

VARIETY OF ROSE

George C. Thomas, Jr., deceased, Beverly Hills, Calif., by Josephine Moorhead Thomas Gardner and George C. Thomas, 3rd, of Beverly Hills, Calif., executors, assignors to Armstrong Nurseries, Ontario, California Application February 24, 1934, Serial No. 712,840

1 Claim. (Cl. 47—61)

This new variety of rose belongs to the class known as Dwarf Polyantha. It is the result of careful breeding efforts carried on by the inventor and it grew from the seed contained in a seed pod obtained by crossing the rose Dorothy Howarth and the rose Perle d'Or. This new variety has been reproduced by budding, in considerable quantity.

Among the more notable features that clearly distinguish this variety from all others and which virtually place it in a distinct class, rather than merely as a distinct variety, are (1) its everblooming habit, (2) its glossy evergreen foliage which does not drop off and leave the plant bare at certain seasons as is common in other polyantha roses, and (3) its single, five-petaled, pure white flowers.

The accompanying illustration shows in full color the foliage, buds and flowers of this new variety.

*The plant.*—When properly cared for, grows to a height of 30 to 36 inches and spreads to about the same width. When covered with pure white flowers against the glossy green foliage, the plant is very striking in appearance. It is really an ornamental evergreen shrub as well as a rose.

The plant is hardy on the Pacific Coast and in the Southern States but has not yet been tested in the East.

*The foliage.*—Leaves are medium green in color, very glossy, appearing as though varnished. In the areas where tested the foliage remains green and very abundant throughout the year.

The smaller branches have a reddish tint on the newer wood. This tint is also noticeable, and in the winter months prominent, on the petioles of the newer leaf branches.

The leaflets occur in arrangements of three to six on a single leaf branch. The thorns are very small and infrequent and are found mostly on the leaf branches.

The individual leaves are medium to small in size, rather heavily veined and have serrations of medium size and depth.

Stipules are small, narrow and terminate in non-curled points.

*The buds.*—Long, narrow and quite pointed, the five sepals being considerably longer than the rolled petals in the bud stage, thus overlapping at the end and giving a long pointed effect.

*The flowers.*—Single, five petaled, measuring 3 to 3½ inches across when mature. The color may be described as silvery white.

The center of each flower shows a prominent display of stamens having creamy-yellow filaments mounted by brownish-amber anthers and the pollen cases are brownish-yellow.

The flowers are usually borne in clusters of four or five. But all the buds in a cluster do not open at once, usually opening successively over a period of several days, only one flower of a cluster ordinarily being open at a time. This blooming continues throughout the year in Southern California; the plant is almost never without blossoms even in mid-winter, being quite distinct in this respect.

When each individual blossom reaches maturity it does not fade and droop but drops off cleanly, thus preserving the fresh crisp appearance of the plant at all times.

The blossoms have a very slight fragrance.

Specimens of flowers of this new variety of dwarf polyantha rose can be distinguished from the variety Baby Elegance by the silvery white color effect of its flowers as compared with the yellow-orange or pale orange-yellow of Baby Elegance. Some specimens of Baby Elegance which have petals nearly white in color do not open out so widely nor curl back so far as do the petals of the new variety. Also it is noted that many specimens of Baby Elegance have small appendages on the side edges of the sepals, not found in this new variety. The foliage is also different in form and texture.

Having thus disclosed this invention, we claim:

The variety of Dwarf Polyantha rose herein shown and described, characterized particularly by its single, silvery white, clusters of flowers continuously produced, its glossy evergreen foliage, and other desirable qualities as described.

JOSEPHINE MOORHEAD
THOMAS GARDNER,
GEORGE C. THOMAS, 3D,
*Executors of the Estate of George C. Thomas, Junior, Deceased.*